United States Patent [19]

Ishihara et al.

[11] Patent Number: 5,607,970
[45] Date of Patent: Mar. 4, 1997

[54] ACAT INHIBITORY AGENT

[75] Inventors: Kazuoki Ishihara, Kamakura; Ryouiti Shin, Sagamihara, both of Japan

[73] Assignee: Kabushiki Kaisya Advance, Tokyo, Japan

[21] Appl. No.: 969,818

[22] PCT Filed: Jul. 6, 1992

[86] PCT No.: PCT/JP92/00857

§ 371 Date: Feb. 1, 1993

§ 102(e) Date: Feb. 1, 1993

[87] PCT Pub. No.: WO93/02185

PCT Pub. Date: Feb. 4, 1993

[30] Foreign Application Priority Data

Jul. 19, 1991 [JP] Japan ................................ 3-203530

[51] Int. Cl.$^6$ ............................. A61K 31/22; A61K 31/20
[52] U.S. Cl. ............................................ 514/546; 514/560
[58] Field of Search ...................................... 514/546, 560, 514/549, 552

[56] References Cited

U.S. PATENT DOCUMENTS 4,272,528  6/1981  Von Esch et al. ...................... 514/119

FOREIGN PATENT DOCUMENTS

A-0014910  9/1980  European Pat. Off. .
A-0104043  3/1984  European Pat. Off. .
2935546    3/1981  Germany .
42-15730   8/1967  Japan .
52-114059  9/1977  Japan .
1516489    7/1978  United Kingdom .

OTHER PUBLICATIONS

Journal of Biological Chemistry, vol. 254, No. 5 (1979), pp. 1534–1536, Susanne Bennett Clark, "Mucosal Coenzyme A–dependent Cholesterol Esterification after Intestinal Perfusion of Lipids in Rats".

Proceedings of the Society for Experimental Biology and Medicine, vol. 177, No. 1 (1984), pp. 188–196, L. L. Gallo et al., "Rat Intestinal Acyl Coenzyme A: Cholesterol Acyl Transferase Properties and Localisation".

Journal of Biological Chemistry, vol. 265, No. 14 (1990), pp. 8042–8051, I. Tabas et al., "Rabitt and Human Liver Contain a Novel Pentacyclic . . . ".

Journal of Lipid Research, vol. 24, (1983), pp. 1127–1134, J. Heider et al., "Role of Acyl CoA:cholesterol Acyltransferase in cholesterol . . . ".

*Primary Examiner*—Kevin E. Weddington
*Attorney, Agent, or Firm*—Finnegan, Henderson, Farabow, Garrett & Dunner

[57] ABSTRACT

An ACAT inhibitory method and composition containing a monoacylglycerol (monoglyceride) as an active ingredient.

3 Claims, No Drawings

ACAT INHIBITORY AGENT

TECHNICAL FIELD

This application is a 371 of PCT/JP92/00857 filed Jul. 06, 1992.

The present invention relates to a novel inhibitory agent for an ACAT enzyme, and more specifically, it relates to a lipid absorption inhibitory edible composition, etc., containing an inhibitory agent for an ACAT enzyme derived from a food component.

BACKGROUND ART

The absorption of a lipid, particularly cholesterol, is believed to be rate determined by a process wherein free cholesterol is converted to ester cholesterol by an ACAT (AcylCoA-Cholesterolacyltransferase) in small intestine epithelial cells. An ACAT inhibitory agent has been found to be useful as an anti-cholesterol agent in this respect. At present, several of these agents are being developed as pharmaceuticals.

DISCLOSURE OF THE INVENTION

As a result of earnest efforts pertaining to the above, the inventors of the present invention found that monoacylglycerol (monoglyceride), a certain kind of fatty acid-like substance derived from microorganism lipids, such as that from lactic acid bacteria and decomposition products of rice bran and wheat bran lipid, demonstrates remarkable inhibitory activity against said enzyme, as those suitable for common use as a so-called functional food component and so forth, and, as a result, the present invention has completed.

Accordingly, in consideration of the present state of the above-mentioned prior art, an object of the present invention is to provide a compound having a remarkable ACAT inhibitory activity, despite being derived from edible natural substances and being essentially non-toxic, as well as an edible composition containing said compound as the active ingredient.

In accordance with the present invention, there are provided an ACAT inhibitory agent containing monoacylglycerol (monoglyceride) as an active ingredient, and a lipid absorption inhibitory edible composition containing the ACAT inhibitory agent and an edible carrier. Although there is no particular limitation to the content of monoacylglycerol (monoglyceride) in the composition, a content of 0.5 to 3% by weight is preferable. Specific examples of the edible carrier include hydroxypropylmethyl cellulose phthalate and casein.

BEST MODE FOR CARRYING OUT THE INVENTION

The present invention will now be explained in detail.

Fatty Acid-like Substance

Those present in microorganism lipids such as those of lactic acid bacteria, and hydrolyzed (enzyme) decomposition products of vegetable lipids such as rice bran and wheat bran lipids, which is purified and isolated in a conventional manner, or commercially available monoacylglycerols (monoglycerides) having 22 carbon atoms or less, preferably 16 carbon atoms or less, such as 2-oleylglycerol, 1-oleylglycerol, 1-linoleylglycerol, 1-linolenoylglycerol, 1-stearoylglycerol, 1-palmitoylglycerol or 1-palmitooleylglycerol, exhibit fatty acid-like properties.

Method of Use and Dosage

The above-mentioned substances can usually be orally administered in a dosage of about 0.1–10 mg/kg (body weight) per day in ordinary form such as tablet or capsule. Since these substances are food components, they are essentially non-toxic when taken orally. On the other hand, in the case of providing same in the form of an edible composition, these substances need not be particularly isolated for utilization, and may be utilized as food auxiliary components such as a microorganism lipid, or the lipid decomposition products of rice bran or wheat bran.

Method for Assaying ACAT Activity

An ACAT activity was assayed according to the method of Heider et al (J. Lipid. Res. 24, 1127–1134 (1983)). That is, a rabbit is fed a 1% cholesterol diet for 3 weeks followed by dissection and extraction of the small intestine. After peeling off the small intestine epithelium and crushing with a homogenizer, incompletely crushed solids are removed by centrifugal separation. The microsome fraction of the 107,000× g sediment was suspended in a 0.154M phosphate buffer (pH 7.4), which is then used for ACAT enzyme preparation. The reaction is carried out by adding 18 nmol of bovine serum albumin and 18 nmol of [1-$^{14}$C]oleylCoA (0.018 μCi/nmol) to 0.5 ml of a 0.154M phosphate buffer (pH 7.4), heating for 5 minutes at 37° C. and adding 40 μl of the above-mentioned ACAT enzyme preparation (0.2–0.4 mg as protein). After allowing the reaction to proceed for the prescribed amount of time, 7 ml of a mixture of dichloromethane: methanol (2:1) is added to the reaction mixture and thoroughly mixed. The reaction, is stopped and the dichloromethane layer is removed, after which the cholesterol oleate portion is separated from that fraction by silica gel TLC (developing solution: petroleum ether:diethyl ether=95:5). The separated portion is scraped off and the radioactivity is measured using a liquid scintillation counter to calculate ACAT activity.

Preparation of Monoacylglycerol (Monoglyceride)

The monoacylglycerol (monoglyceride), such as 2-oleylglycerol, 1-oleylglycerol, used in the present invention are known substances that are, for example, commercial reagents available from the Sigma Corp. (the compounds of the present invention used in the following Examples are all reagents of the Sigma Corp.).

EXAMPLES

The present invention will now be further illustrated by, but is by no means limited to, the following Examples.

(1) ACAT Inhibitory Activity of Fatty Acid-Like Substance Monoglycerides (1) In Test Tube

TABLE 1

| Monoglycerides | Inhibitory Ratio (%) Concentration (μg/ml) | | | | |
| --- | --- | --- | --- | --- | --- |
| | 200 | 150 | 100 | 50 | 20 |
| 2-oleylglycerol | 100 | 94 | 82 | 62 | 32 |
| 1-oleylglycerol | 100 | 92 | 81 | 59 | 30 |
| 1-linoleylglycerol | 93 | 86 | 74 | 54 | 28 |
| 1-linolenoylglycerol | 92 | 86 | 76 | 50 | 25 |
| 1-stearoylglycerol | 49 | 45 | 38 | 29 | 15 |
| 1-palmitoylglycerol | 94 | 86 | 75 | 56 | 26 |
| 1-palmitooleylglycerol | 91 | 84 | 72 | 53 | 24 |

(2) Animal Test

A test substance according to the present invention was administered to hamsters (males, body weight: 100 g) at a dose of 1 mg/animal/day by mixing in the same to their feed. The ACAT activity of small intestine epithelial cells was then measured after one week and after two weeks. The results are indicated in Table 2.

TABLE 2

| Monoglycerides | ACAT Inhibitory Ratio (%) | |
|---|---|---|
|  | After 1 week | After 2 weeks |
| 2-oleylglycerol | 64 | 56 |
| 1-oleylglycerol | 60 | 52 |
| 1-linoleylglycerol | 59 | 53 |
| 1-linolenoylglycerol | 57 | 51 |
| 1-stearoylglycerol | 31 | 29 |
| 1-palmitoylglycerol | 56 | 50 |
| 1-palmitooleylglycerol | 57 | 54 |

INDUSTRIAL APPLICABILITY

As mentioned in detail above, the ACAT inhibitory agent of the present invention containing a monoacylglycerol (monoglyceride) as an active ingredient is substantially non-toxic since it is derived from edible natural substances. Moreover, since it demonstrates remarkable ACAT inhibitory activity, it can be suitably used in functional food components and so forth.

We claim:

1. An ACAT inhibitory composition containing as an active ingredient from 0.5 to 3% by weight, based on the total weight of the composition, of a monoacylglycerol selected from the group consisting of 1-stearoylglycerol, 1-palmitoylglycerol and a mixture thereof and an acceptable carrier therefor.

2. A lipid absorption inhibitory edible composition containing an ACAT inhibitory amount of from 0.5 to 3% by weight, based on the total weight of the composition, of a monoacylglycerol selected from the group consisting of 1-stearoylglycerol, 1-palmitoylglycerol and a mixture thereof and an edible carrier therefor.

3. A method for inhibiting the absorption of lipids in persons, which comprises administering to a person in need thereof an ACAT inhibitory composition containing as the active ingredient from 0.5 to 3% by weight, based on the total weight of the composition, of a monoacylglycerol selected from the group consisting of 1-stearoylglycerol, 1-palmitoylglycerol and a mixture thereof and an acceptable carrier therefor.

* * * * *